(12) United States Patent
Hector et al.

(10) Patent No.: US 8,748,152 B1
(45) Date of Patent: Jun. 10, 2014

(54) PREVOTELLA RUMINICOLA XYLOSE ISOMERASE AND CO-EXPRESSION WITH XYLULOKINASE IN YEAST FOR XYLOSE FERMENTATION

(75) Inventors: Ronald E. Hector, Washington, IL (US); Bruce S. Dien, Peoria, IL (US); Michael A. Cotta, Edelstein, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/616,629

(22) Filed: Sep. 14, 2012

(51) Int. Cl.
*C12N 9/92* (2006.01)

(52) U.S. Cl.
USPC .......................................................... 435/234

(58) Field of Classification Search
None
See application file for complete search history.

(56) References Cited

U.S. PATENT DOCUMENTS

| 7,622,284 B2 | 11/2009 | Op Den Camp et al. |
| 2006/0234364 A1 | 10/2006 | Rajgarhia et al. |
| 2010/0112658 A1 | 5/2010 | Hughes et al. |

OTHER PUBLICATIONS

Hughes, Stephen R., et al., "Engineered *Saccharomyces cerevisiae* strain for improved xylose utilization with a three-plasmid SUMO yeast expression system", Plasmid, 61, 2009, pp. 22-28.

Matte, Allan, et al., "Enzymes associated with metabolism of xylose and other pentoses by *Prevotella* (Bacteroides) *ruminicola* strains, Selenomonas ruminantium D, and Fibrobacter succinogenes S85", Can. J. Microbiol., vol. 38, 1992, pp. 370-376.

*Primary Examiner* — Suzanne M Noakes
(74) *Attorney, Agent, or Firm* — Elizabeth R. Sampson; Randall E. Deck; John D. Fado

(57) ABSTRACT

A xylose isomerase (XI) enzyme which exhibits increased activity and affinity for xylose is produced by strain TC2-24 of the rumen bacterium, *Prevotella ruminicola*. The gene encoding this enzyme may be used to produce improved recombinant yeast capable of utilizing xylose. The recombinant yeast are preferably transformed with heterologous polynucleotide sequences coding both the *P. ruminicola* XI, and the xylulokinase (XKS) of a *Prevotella* species. Yeast transformed with the polynucleotide sequences coding both of these XI and XKS exhibit significantly increased xylose utilization and cell growth on a culture medium containing xylose as the sole carbon source, in comparison to yeast transformed with XKS and XI from other sources.

14 Claims, 8 Drawing Sheets

```
  1  makeyfpftg  kipfegkdsk  nvmafhyyep  ekvvmgkkmk  dwlkfamaww 51  htlggasadq  fggqtrsyew  dkaadavqra  kdkmdagfei  mdklgieyfc 101  fhdvdlveeg  etiaeyerrm  keitdyalvk  mkeypnikll  wgtanvfgnk 151  ryangastnp  dfdvvaraiv  qiknaidati  klggtnyvfw  ggregymsll 201  ntdqkrekeh  matmltmard  yarakgfkgt  fliepkpmep  skhqydvdte 251  tvcgflrahg  ldkdfkvnie  vnhatlaght  fehelacavd  ngmlgsidan 301  rgdaqngwdt  dqfpidnfel  tqamleiirn  gglgnggtnf  dakirrnstd 351  ledlfiahis  gmdamaralm  naaaileese  lpkmkkerya  sfdngigkdf 401  edgkltleqa  yeygkkveep  kqtsgkqeky  ettvalyck
```

Figure 1

```
   1 atggcaaaag agtatttccc gtttaccggt aaaattcctt tcgagggaaa ggacagtaag
  61 aatgtaatgg ctttccacta ttacgagcct gagaaggtcg tgatgggaaa gaagatgaag
 121 gactggctga agttcgctat ggcttggtgg catacactgg gtggcgcttc tgctgaccag
 181 tttggtggtc agactcgttc ttatgagtgg gataaggctg ctgacgccgt tcagcgcgca
 241 aaggataaga tggacgctgg ttttgagatc atggacaagc tgggtatcga gtacttctgc
 301 ttccacgatg ttgacctcgt tgaagagggt gagacgatcg ctgagtacga gcgtcgcatg
 361 aaggagatca cagactacgc tctggtgaag atgaaggaat atcccaacat caagctcctc
 421 tggggtacag ctaacgtatt tggcaacaag cgctatgcaa atggtgcttc taccaaccct
 481 gatttcgacg ttgtggctcg cgccatcgtt cagatcaaga cgctatcga tgctaccatc
 541 aagttgggtg gtaccaacta tgtattctgg ggcggtcgtg agggttatat gagccttctg
 601 aacactgacc agaagcgtga aggagcac atggcaacca tgctgaccat ggctcgcgac
 661 tacgctcgcg ctaagggctt caagggtacg ttcctgattg agccgaagcc catggagcct
 721 tcaaagcacc agtacgatgt tgacactgag accgtatgcg gtttcctccg tgctcatggt
 781 ctggacaagg acttcaaggt gaacatcgag gtaaaccacg ctactctggc aggtcacacc
 841 ttcgagcacg agctggcttg cgctgtcgac aacggtatgc tcggttctat cgacgctaac
 901 cgtggtgatg ctcagaacgg ttgggatact gaccagttcc ccatcgacaa cttcgagctg
 961 acacaggcta tgctggagat catccgcaat ggtggtctgg caatggcgg taccaacttc
1021 gacgctaaga tccgtcgtaa ctctaccgac ctcgaggatc tcttcatcgc tcacatcagc
1081 ggtatggatg ctatggcacg cgccctgatg aatgctgctg ctatcctgga ggagagcgag
1141 ctgccgaaga tgaagaagga gcgttatgct tcattcgaca acgtattgg taaggacttc
1201 gaggatggca agctgactct cgagcaggct tacgagtacg gtaagaaggt tgaggagccc
1261 aagcagactt ctggtaagca ggagaagtac gagaccaccg tagcacttta ctgcaagtaa
```

Figure 2

```
   1 atggccaaag agtacttccc attcaccgga aagataccat tcgaaggcaa agattccaaa
  61 aacgtgatgg cctttcacta ttacgaacca gaaaaagtcg ttatgggcaa aaagatgaaa
 121 gattggctga aattcgccat ggcttggtgg catacactag gtgcgcatc tgcagaccaa
 181 ttcggaggtc aaactagatc ttatgaatgg gataaagcag ctgacgctgt acagagagca
 241 aaagataaga tggatgcagg gttcgagatc atggataagc ttggtattga atactttgt
 301 tttcatgacg ttgacttagt ggaggaaggc gagactattg cagagtacga acgtagaatg
 361 aaggaaatca ctgattatgc tttagtcaag atgaaggaat acccaaacat taagttgttg
 421 tggggacag ctaatgtttt tggcaacaaa agatacgcta atggagcctc aacaaatcct
 481 gattttgatg tagttgccag ggccatcgtt caaatcaaaa acgcaattga cgcaacaatc
 541 aaattgggag gtacaaacta cgttttctgg ggtggaaggg agggttacat gtcattgctg
 601 aatactgatc agaaaagaga aaaggaacat atggccacta tgcttactat ggccagagac
 661 tacgcaagag ctaagggttt caagggtact tttctaattg agcctaaacc tatggaacct
 721 tctaaacatc aatacgatgt agataccgag acagtctgtg gttttctaag agctcacggc
 781 ttagataaag actttaaggt aaacattgaa gttaatcacg caactctggc tggtcataca
 841 tttgagcatg aattggcatg tgctgtggac aatggaatgc ttggctctat cgatgcaaat
 901 agaggtgacg cacaaaatgg gtgggatacc gatcagtttc caatcgacaa ctttgaacta
 961 actcaagcaa tgttggaaat cattagaaat ggggattag gtaatggtgg aacaaacttt
1021 gatgctaaga tacgtagaaa ttccacagac ttggaagatt tgttcatagc tcacattagt
1081 ggcatggatg ctatggcaag agccctaatg aacgctgctg caatacttga ggaatcagaa
1141 ttgccaaaga tgaaaaagga gagatatgct tcatttgaca atggtatcgg taaagatttc
1201 gaagatggta aacttacatt agaacaagct tacgaatatg gcaaaaggt tgaggaacca
1261 aagcaaacct ctggtaaaca agagaaatac gaaacaaccg tggccctgta ttgcaagtaa
```

Figure 3

```
  1  manryllgfd  vgsssvkasl  vnadsgkcva  tafypekeap  imavkagwae
 51  qdpqmwwdna  klslqkimke  sgataeeika  vgisyqmhgl  vcvdkdlkal
101  rpaiiwcdsr  avpygekafk  dlgadkclsh  llnspgnfta  aklawvkene
151  pelyskiykv  mlpgdyiamr  lsgvanttvs  glsegmfwdf  knnqvadflm
201  dyygfdhsli  adivptfaeq  svvsaeaaae  mglkagtpit  yrggdqpnna
251  lslnvlnpge  iaatagtsgv  vygvlgdvny  dpqirvntfa  hvnhtadqtr
301  lgvllcingt  gilnawthrn  itpeigyaem  ndlaasvpig  segvtvipfg
351  ngaervlenk  eigcsingln  fnkhnkahlv  raaqegivfs  fcygmeimqq
401  mgmdikkiha  gkanmflspl  frntlagvsg  atielydtdg  svgaakgagl
451  gagiyanase  afasldklev  iepdaqnraa  yraayeawke  tlkknm
```

Figure 4

```
   1 atggcaaata gatatctatt aggttttgat gtcggtagct catcagtgaa ggcatcgttg
  61 gttaacgccg atagcggcaa gtgtgtggca acagcttttt atcctgaaaa ggaggctcct
 121 attatggctg taaaggctgg atgggcagag caggatccac agatgtggtg ggataatgcc
 181 aaattgagtc tgcagaagat tatgaaagag agtggtgcta cagctgagga gattaaggct
 241 gtgggtatct cgtatcagat gcacggtttg gtttgtgtag ataaggatct gaaggcattg
 301 cgtccagcta ttatttggtg cgactcacgt gctgtacctt atggcgagaa ggctttcaag
 361 gatctcggtg ctgacaagtg cttgagtcat ctgttgaatt caccaggaaa ctttaccgct
 421 gccaagttgg cttgggtaaa agaaaatgaa ccagaactct atagtaaaat ataaggta
 481 atgctgcctg gtgattatat cgctatgcga ctgagtggtg ttgctaatac cactgtcagc
 541 ggtctgtcag agggtatgtt ctgggatttc aagaataatc aggtggctga cttcttgatg
 601 gattactatg gattcgatca ttcgctgatt gctgatatcg ttccaacctt tgctgagcag
 661 agcgtagtaa gtgcagaagc tgctgctgag atgggcctga agctggtac tcctatcacc
 721 tatagaggtg gtgaccagcc aaacaatgcg ctctcgctga atgtgctgaa tcctggtgag
 781 attgctgcaa ctgcaggtac atcgggtgtg gtttatggtg tacttggtga tgtgaactac
 841 gatccacaga tccgtgtaaa tacttttgca catgtgaatc atacagcaga ccagactcgt
 901 ctgggagtgc tgctttgtat taatggtact ggtattttga atgcttggac tcatcgtaat
 961 atcacgcctg agattggcta tgccgagatg aacgatctgg ctgccagtgt gcccattggt
1021 agtgagggcg tgactgtaat tccattcgga aatggtgcta gcgcgtatt ggagaacaag
1081 gagattggtt gttctatcaa tggcttgaac tttaataagc ataacaaggc tcacttggtt
1141 cgtgctgctc aggagggtat cgtattctca ttctgctatg gtatggagat tatgcagcag
1201 atgggtatgg atattaagaa gattcacgct ggtaaggcta acatgttctt gagtccattg
1261 ttccgtaata cattggctgg tgtgagtggt gcaaccatcg aactgtatga tacagatggt
1321 tcggtaggtg ccgccaaggg tgctggctta ggtgctggca tctatgctaa tgcttctgag
1381 gcttttgctt cgctggataa gttggaggtg attgagccag atgctcagaa ccgcgctgct
1441 taccgtgctg cctatgaggc ttggaaagaa accttgaaaa agaatatgta a
```

Figure 5

```
   1 atggcaaaca gatacttgct ggggttcgat gttggttcct ctagtgtaaa agcatcttta
  61 gttaacgctg atagtgggaa atgtgtagca acagcattct atccagaaaa ggaagctcct
 121 atcatggctg ttaaagcagg atgggctgaa caagatccac aaatgtggtg ggataatgcc
 181 aagttgtctt tacagaaaat catgaaggaa tccggagcta cagccgagga gattaaggcc
 241 gttggcatat cataccaaat gcatggattg gtttgcgtag ataaagatct aaaagctcta
 301 cgtcctgcaa tcatttggtg tgactccaga gctgtcccat atggtgaaaa agcctttaag
 361 gacttaggtg ccgataagtg tttgtcacat ttgttaaaca gtccaggcaa tttcacagca
 421 gctaagttag cctgggtaaa ggaaaatgaa ccagaattgt actcaaagat atacaaagtc
 481 atgctaccag gtgattacat cgcaatgaga ctttctgggg tagcaaatac tacagtgtct
 541 ggattatctg aaggaatgtt ttgggatttc aaaaacaatc aagtagctga ctttctgatg
 601 gactatacg gttttgacca ttcacttatt gctgatatag tccctacttt tgcagaacaa
 661 tcagtcgtat ctgccgaggc agccgcagaa atgggtctaa aggcaggtac tcctattacc
 721 tatagaggtg gcgatcaacc taacaatgct ttaagtttga acgtgcttaa tccaggtgag
 781 attgctgcca cagctggtac atctggtgtt gtgtatggtg ttttaggtga cgtgaattac
 841 gatccacaga taagagtgaa tacttttgcc cacgttaatc ataccgctga ccagactagg
 901 ttaggtgttc tgctttgtat caacggaaca ggcatcctga atgcctggac acatagaaac
 961 attactccag aaataggtta cgctgaaatg aacgatctag ctgcttcagt accaattggg
1021 tctgagggcg ttacagttat cccattcggt aatggagctg aaagggtctt ggagaataag
1081 gaaatagggt gttcaatcaa tggtctgaac tttaacaaac acaacaaagc tcaccttgtg
1141 agagccgctc aggaaggaat agtctttca ttttgctatg gtatggaaat catgcaacaa
1201 atgggaatgg acatcaaaaa gattcatgcc ggaaaagcaa acatgttcct atctcctttg
1261 tttagaaata ctttagctgg agtttcagga gctaccattg agttatacga cacagatggt
1321 tccgttggcg cagcaaaagg cgcaggcttg ggtgccggca tctacgccaa tgcatctgaa
1381 gctttcgctt ctcttgataa acttgaagtg atcgaacctg acgctcaaaa cagagccgct
1441 tatagagccg catacgaagc atggaaagag actttgaaaa agaacatgta a
```

Figure 6

PREVOTELLA RUMINICOLA XYLOSE ISOMERASE AND CO-EXPRESSION WITH XYLULOKINASE IN YEAST FOR XYLOSE FERMENTATION

BACKGROUND OF THE INVENTION

1. Field of the Invention

The invention is drawn to a novel xylose isomerase enzyme and recombinant yeasts which are able to utilize xylose.

2. Description of the Prior Art

Over 95% of U.S. fuel ethanol is produced using corn. Eventually, it is envisioned that annual corn ethanol production can expand to 12-15 billion gallons, consuming 31% or more of the corn harvest. For this reason, commercializing lignocellulose as a feedstock for further ethanol production has been made a national priority. Despite a growing commitment by industry to move towards these more challenging feedstocks, technical barriers still remain unsolved. One critical need is for more robust microbial strains capable of fermenting the more diverse mixture of neutral sugars released by hydrolysis of lignocellulose. Plant cell wall lignocellulose contains, in order of relative abundance, glucose, xylose, arabinose, galactose, and miscellaneous other sugars. While *Saccharomyces* strains ferment hexoses, they do not ferment the pentose sugars arabinose or xylose.

Several yeast, such as *Pachysolen tannophilus*, *Scheffersomyces stipitis*, and *Candida shehatae* naturally ferment xylose. While some of these are being pursued for commercialization, they have several defects, including the inability to grow anaerobically on xylose, low tolerance to acetic acid and other inhibitory chemicals common to biomass hydrolysates, and generally low productivity and yields compared to glucose-fermenting *Saccharomyces cerevisiae*. Attention in recent years has turned to engineering bacteria to selectively produce ethanol (Dien et al., 2003, Appl. Microbiol. Biotechnol., 63:258-266), improving the performance of native xylose-fermenting yeast (Jeffries, 2006, Curr. Opin. Biotechnol., 17:320-326), or engineering *Saccharomyces* strains to ferment pentose sugars, especially xylose (Hahn-Hägerdal et al., 2007 Appl. Microbiol. Biotechnol., 74:937-953; Van Maris et al., 2006, Antonie van Leeuwenhoek, 90:391-418; Karhumaa et al., 2005, Yeast, 22:359-368; Kuyper et al., 2004, FEMS Yeast Res. 4:655-664; and Kuyper et al., 2005, FEMS Yeast Res., 5:399-409).

*Saccharomyces* yeast can naturally utilize the pentose phosphate pathway intermediate xylulose. Genetic strategies to enable the yeast to ferment xylose have centered on introducing the needed activities for converting xylose to xylulose. Naturally xylose-fermenting yeasts convert xylose into xylitol using xylose reductase (XR) and xylitol into xylulose using xylitol dehydrogenase (XDH), but the process gives rise to a cofactor imbalance that results in production of xylitol (Van Maris et al., 2006, ibid; Kuyper et al., 2004, ibid). *Saccharomyces* yeast strains have been engineered that functionally express XR and XDH genes (Jeffries and Jin, 2004, Appl. Microbiol. Biotechnol., 63:495-509), and several have reasonable ethanol yields and reduced xylitol production, conceivably because enough oxygen enters the system to regenerate NAD+ from NADH via respiration instead of xylitol production (Karhumaa et al., 2005, ibid; Van Maris et al., 2006, ibid). Precisely controlled oxygen levels are nearly impossible to maintain in large-scale industrial operations, which limits the intermediate potential of these biocatalysts.

In an effort to convert xylose to xylulose without creating cofactor imbalances, *Saccharomyces* yeast strains were engineered to express a heterologous xylose isomerase (XI), which catalyzes this conversion directly (Karhumaa et al., 2005, ibid; Walfridsson et al., 1996, Appl. Environ. Microbiol., 62:4648-4651). However the activity of the XI enzyme was too low for efficient xylose metabolism. It was discovered that the xylose isomerase from *Piromyces* sp. E2 can be expressed at sufficient levels in *S. cerevisiae* (Harhangi et al., 2003, Arch. Microbiol., 180:134-141; Kuyper et al., 2004, ibid). After evolutionary engineering and expression of all genes encoding for the enzymes involved in the conversion of xylose into intermediates of glycolysis in addition to expression of XI and deletion of the gene encoding aldose reductase (to reduce production of the unwanted side product xylitol), a *Saccharomyces* strain was constructed that had an ethanol production rate of 0.46 g per g xylose per hour under anaerobic batch cultivation on xylose. When grown on 20 g per liter glucose and xylose each, an exponential glucose consumption phase followed by a slower, almost linear, xylose consumption phase was observed (Kuyper et al., 2005, ibid). Further selection for xylose growth yielded a strain that when cultivated in anaerobic batch culture with 20 g per liter glucose and xylose each, fermented all sugars in 24 hours, an improvement of 20 hours over the strain before selection. On xylose alone it had an ethanol production rate of 0.49 g per g xylose per hour under anaerobic batch cultivation (Van Maris et al., 2006, ibid). Growth in anaerobic xylose cultures is considered a highly desirable quality in industrial fermentation since it maintains cell viability and greatly increases the specific rate of ethanol production. Although uptake kinetics were also improved, the engineered *Saccharomyces* strains are only now moving towards commercialization (Hahn-Hägerdal et al., 2007, ibid). Co-fermentation of hexose and pentose sugars is still a major challenge.

More recently, Hughes et al. (U.S. patent application Ser. No. 12/568,071; 2008, Plasmid, 61:22-38) disclosed that recombinant *S. cerevisiae* produced by transformation of the yeast with heterologous polynucleotide sequences coding for XI and a xylulokinase (XKS) from *Yersinia pestis* exhibited high growth rates on media with xylose as the sole carbon source.

However, despite these and other advances, the need remains for improved enzymes and yeast for utilizing xylose.

SUMMARY OF THE INVENTION

We have now discovered a novel xylose isomerase (XI) enzyme which exhibits increased catalytic activity and affinity for xylose. The XI is produced by strain TC2-24 of the rumen bacterium, *Prevotella ruminicola*. The gene encoding the enzyme has also been isolated from this strain, and may be used to produce improved recombinant yeast capable of utilizing xylose. In a preferred embodiment, the yeast strains are transformed with heterologous polynucleotide sequences coding not only the *P. ruminicola* XI, but also the xylulokinase (XKS) of a *Prevotella* species. We have further discovered that yeast transformed with the polynucleotide sequences coding both of these XI and XKS exhibit significantly increased xylose utilization and cell growth on a culture medium containing xylose as the sole carbon source, in comparison to yeast transformed with XKS and XI originating from other sources.

In accordance with this discovery, it is an object of this invention to provide a novel xylose isomerase exhibiting increased activity and affinity for xylose.

Another object of this invention is to provide polynucleotide sequences encoding the novel xylose isomerase exhibiting increased activity and affinity for xylose.

A further object of this invention is to provide recombinant yeast that are effective for utilization of xylose.

A still further object of this invention is to provide improved recombinant yeast that are effective for use in the production of ethanol.

Other objects and advantages of this invention will become readily apparent from the ensuing description.

BRIEF DESCRIPTION OF THE DRAWINGS

FIG. 1 shows the predicted amino acid sequence (SEQ ID NO: 1) of the XI produced by *P. ruminicola* strain TC2-24.

FIG. 2 shows the DNA sequence (SEQ ID NO: 2) of the open reading frame of the XI gene produced by *P. ruminicola* strain TC2-24.

FIG. 3 shows DNA sequence (SEQ ID NO: 3) encoding the XI produced by *P. ruminicola* strain TC2-24, optimized for expression in *S. cerevisiae*.

FIG. 4 shows the predicted amino acid sequence (SEQ ID NO: 4) of the XKS produced by *P. ruminicola* strain 23.

FIG. 5 shows the DNA sequence (SEQ ID NO: 5) of the open reading frame of the XKS gene produced by *P. ruminicola* strain 23.

FIG. 6 shows DNA sequence (SEQ ID NO: 6) encoding the XKS produced by *P. ruminicola* strain 23, optimized for expression in *S. cerevisiae*.

DEFINITIONS

Figure 7:
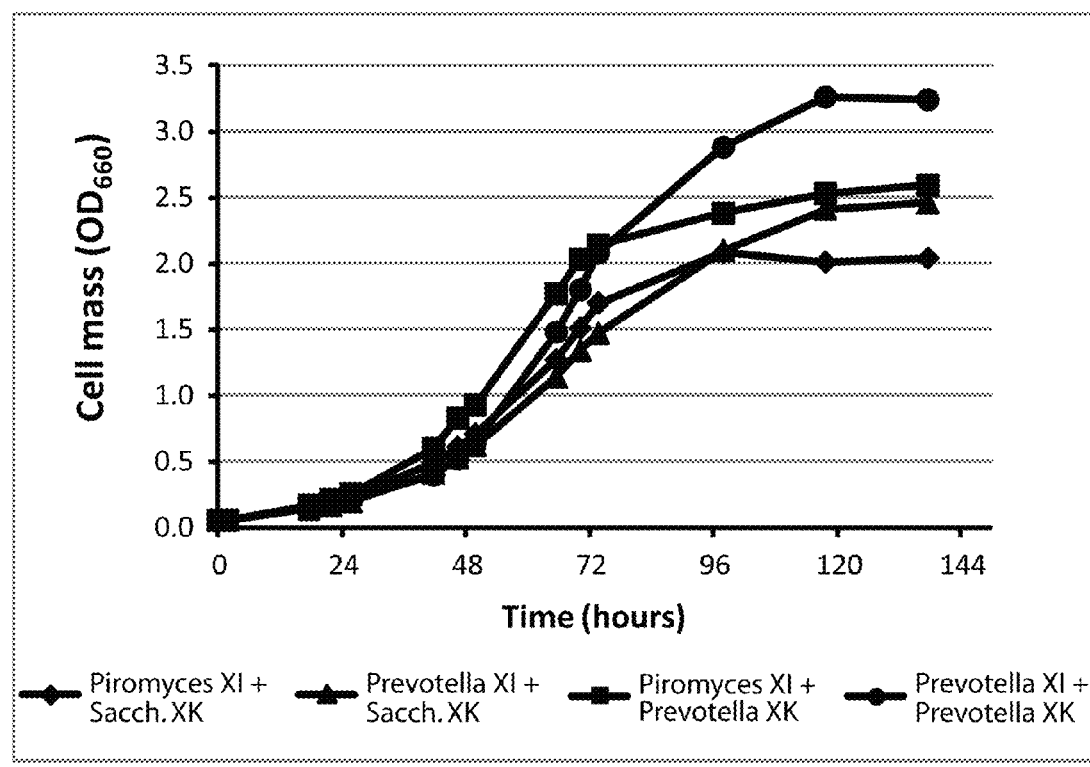
FIG. 7 shows the growth on xylose medium by recombinant *S. cerevisiae* expressing the *P. ruminicola* XI and XKS, compared to recombinants expressing XI and XKS from other sources, as described in Example 1.

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eukaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses. Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism, a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bends between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Stringent Hybridization Conditions. The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will differ in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent hybridization conditions comprise hybridization in 50% formamide, 1 M NaCl, 1% SDS at 42° C., and a wash in 0.1×SSC at 60 to 65° C. It is also understood that due to the advances in DNA PCR and sequencing approaches that issues of gene identity and homology may be determined by sequence based rather than hybridization approaches.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In procaryotes and some fungi, for example, the exogenous DNA may be maintained on an episomal element such as a plasmid. With respect to most eukaryotic cells, a stably transformed cell is one in which the exogenous DNA has been integrated into a chromosome so that it is inherited by daughter cells through chromosome replication. This stability is demonstrated by the ability of the eukaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION OF THE INVENTION

In the following description, the nomenclature used to define the proteins and peptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The XI described herein is produced by and isolated from *P. ruminicola* strain TC2-24, and is a D-xylose aldose ketose isomerase (EC 5.3.1.5) which is effective for the enzymatic conversion of xylose to xylulose. In contrast with other previously described XI, the XI produced by *P. ruminicola* strain TC2-24 exhibits unexpectedly high activity and affinity for xylose. For instance, the previously described XI produced by *Piromyces* sp. E2 exhibits a Michaelis-Menten constant, $K_m$, for xylose of 46 mM and a $V_{max}$ of 0.26 U/mg (measured from a cell extract, at 25° C. and a pH of 7.5), while the codon-optimized XI of *P. ruminicola* strain TC2-24 (SEQ ID NO: 3) expressed in a strain of *S. cerevisiae* exhibits a $K_m$ for xylose of 41 mM and a $V_{max}$ of 0.14 U/mg (also measured from a cell extract, at 25° C. and a pH of 7.5). Moreover, when recombinant XI of *P. ruminicola* strain TC2-24 is expressed from a strain of *S. cerevisiae* and further adapted for improved xylose fermentation, also using the codon-optimized sequence for the XI described above, the XI exhibits a $K_m$ for xylose of 29 mM and a $V_{max}$ of 0.82 U/mg (also measured from a cell extract, at 25° C. and a pH of 7.5). The enzyme has been isolated, substantially free from other proteins or cell components which are normally present in the cells of the bacterium, such that the XI is the only significant protein or peptide in the sample and may be used effectively as an enzyme for conversion of xylose to xylulose. Moreover, the enzyme has been produced in recombinant form as described herein below. Thus, the term "isolated" encompasses not only enzyme which has been recovered from naturally occurring cells, but also recombinant enzyme and synthesized enzyme. The amino acid sequence of the isolated XI of *P. ruminicola* strain TC2-24 has been determined and is shown in FIG. 1 and is provided as SEQ ID NO: 1.

The gene encoding the XI of *P. ruminicola* strain TC2-24 has also been isolated, cloned and sequenced. The nucleic acid sequence of the open reading frame of the gene is shown in FIG. 2 and is provided as SEQ ID NO: 2. As used herein, isolated nucleic acid sequences refer to sequences which have been substantially separated from other nucleic acids or cell components which are normally present in the cells of the bacterium, such that the XI encoding sequences are the only significant sequences in the sample that can be used to express or produce the XI in a host cell as described below. The term encompasses not only nucleic acid sequences which have been recovered from naturally occurring cells, but also recombinant or cloned nucleic acid sequences, and synthesized nucleic acid sequences. The nucleic acid sequences may be recovered from cells of *P. ruminicola* strain TC2-24, for example, by constructing a genomic DNA or cDNA library and screening for the XI nucleic acid using the disclosed sequences as probes. However, in a preferred embodiment, the sequences are synthesized using techniques established in the art for automated DNA synthesis or amplification. As used herein, the nucleic acid sequences of the XI encompass either or both of the coding strand or its complement.

Because of the degeneracy of the genetic code, there exists a finite set of nucleotide sequences which can code for a given amino acid sequence. Consequently, nucleic acids may be identical in sequence to the sequence which is naturally occurring or they may include alternative codons which encode the same amino acid as that which is found in the naturally occurring sequence. Furthermore, nucleic acids may include codons which represent conservative substitutions of amino acids as are well known in the art. Further still, different species can preferentially use different codons to code for the same amino acid and significant differences in tRNAs can exist. Thus, translation of recombinant proteins can often be enhanced by optimizing codon usage to the preferred codons used by the expression species. It is understood that all such equivalent sequences are operable variants of the disclosed XI gene sequence, since all give rise to the same XI enzyme (i.e., the same amino acid sequence) during in vivo transcription and translation, and are hence encompassed herein. By way of example and without being limited thereto, a preferred codon-optimized sequence effective for enhancing translation of the XI in *Saccharomyces cerevisiae* is shown in FIG. 3, and is provided as SEQ ID NO: 3. DNA sequences which contain significant sequence similarity to the coding regions of the nucleotide sequence of SEQ ID NOs: 2 and 3 are also encompassed by the invention. As defined herein, two DNA sequences contain significant sequence similarity when at least 85% (preferably at least 90% and most preferably 95%) of the nucleotides match over the defined length of the sequence. Sequences that are significantly similar can be identified in a Southern hybridization experiment under stringent hybridization conditions as is known in the art. See, for example, Sambrook et al., Molecular Cloning: A Laboratory Manual ($2^{nd}$ Ed.), Vol. 1-3, Cold Spring Harbor Laboratory, Cold Spring Harbor, N.Y., 1989, or DNA Cloning: A Practical Approach, Vol. I and II (Ed. D. N. Glover), IRL Press, Oxford, 1985.

The XI enzyme may be produced by the above-mentioned *P. ruminicola* strain TC2-24 or recombinant microorganisms transformed with the *P. ruminicola* strain TC2-24 gene encoding the XI, preferably yeast, such as species selected from *Zygosaccharomyces*, *Brettanomyces* (*Dekkera*), *Schizosaccharomyces*, *Pachysolen*, *Pichia*, *Scheffersomyces*, *Spathaspora*, *Kluyveromyces*, *Debaryomyces*, *Candida*, *Yarrowia*, *Aspergillus*, *Trichoderma*, *Pennicillium*, and more preferably *Saccharomyces*, particularly *S. cerevisiae*. The original source for the XI, *P. ruminicola* strain TC2-24, has been deposited under the provisions of the Budapest Treaty in the Agricultural Research Service Culture Collection (NRRL), 1815 N. University St., Peoria, Ill., 61604, USA, on Aug. 29, 2012, and has been assigned Deposit Accession No. NRRL B-50773. Production of the XI may be accomplished by culture of *P. ruminicola* strain TC2-24 or a recombinant microorganism transformed with the *P. ruminicola* strain TC2-24 gene encoding the XI, using conventional techniques under conditions that are effective to promote growth and XI production. Any number of well-known liquid or solid nutrient media may be used, although xylose is preferably used as the carbon source. Suitable conditions and media will vary with the particular microorganism and may be readily determined by the practitioner skilled in the art. Upon completion of the culture, the XI may be isolated from the cells using techniques conventional in the art, such as by centrifugation or filtration. Purification may be effected, for example, by ultrafiltration, dialysis, ion-exchange chromatography, HPLC, size-exclusion chromatography or electrophoresis, such as polyacrylamide-gel-electrophoresis (PAGE). Using these techniques, XI may be recovered in pure or substantially pure form.

Transformation of yeast with the heterologous polynucleotide sequence encoding the XI of *P. ruminicola* strain TC2-24 confers the ability to utilize and ferment xylose through the conversion of xylose to xylulose (utilizing xylose as the sole carbon source). However, optimal xylose utilization is achieved by the further transformation of the yeast with an additional polynucleotide sequence encoding an XKS enzyme. The source for the XKS is not critical and a variety of genes encoding XKS have been cloned and sequenced which are suitable for use herein, including endogenous yeast XKS or *Yersinia pestis* XKS (described in Hughes et al., U.S. patent application Ser. No. 12/568,071, published as 2010/0112658 A1, the contents of which are incorporated by reference herein). However, in accordance with a preferred embodiment, the XKS is derived from a *Prevotella* species, and most preferably from the same species as the XI, *P. ruminicola*, although the XKS need not be from the same strain. We have discovered that yeast transformed with the polynucleotide sequences coding both of *P. ruminicola* strain TC2-24 XI and *Prevotella* XKS, exhibit significantly increased xylose utilization and cell growth on a culture medium containing xylose as the sole carbon source, in comparison to yeast transformed with XKS and XI from other sources. Without being limited thereto, a particularly preferred XKS for use herein is the XKS of *P. ruminicola* 23, which is recognized as the type strain for this species and is available from the American Type Culture Collection, (10801 University Blvd, Manassas, Va., 20110-2209, USA, as deposit accession no. ATCC 19189). The gene encoding the XKS of *P. ruminicola* 23 has also been isolated, cloned and sequenced. The amino acid sequence of the *P. ruminicola* 23 XKS is shown in FIG. 4 and is provided as SEQ ID NO: 4, while the nucleic acid sequence of the open reading frame of the gene encoding this enzyme is shown in FIG. 5 and is provided as SEQ ID NO: 5. As with the XI gene, all equivalent sequences of the XKS gene are operable variants of this disclosed sequence, since all give rise to the same XKS enzyme (i.e., the same amino acid sequence as SEQ ID NO: 4) during in vivo transcription and translation, and are hence encompassed herein. By way of example and without being limited thereto, a preferred codon-optimized sequence effective for enhancing translation of the XKS in *S. cerevisiae* is shown in FIG. 6, and is provided as SEQ ID NO: 6.

The nucleotide sequences of the XI and XKS can be used to prepare recombinant DNA molecules by cloning into any suitable vector. The nucleotide sequences may be cloned into the same vector, but are preferably cloned into different vectors for ease of selecting their relative copy number per cell, as a higher copy number of XI relative to XKS is preferred. For example, without being limited thereto, the XI is preferably provided at between about 5-50 copies/cell while XKS is preferably provided at between about 1-2 copies/cell. A variety of vector-yeast host cell expression systems may be employed in practicing the invention. Without being limited thereto, strains of *Saccharomyces*, particularly *S. cerevisiae*, are preferred. Thus, vectors used in practicing the present invention are selected to be operable as cloning vectors or expression vectors in the selected yeast host cell. Numerous vectors are known to practitioners skilled in the art, and selection of an appropriate vector and host cell is a matter of choice. The vectors may, for example, be bacteriophage, plasmids, viruses, or hybrids thereof, such as those described in Sambrook et al. [Molecular Cloning: A Laboratory Manual, Cold Springs Harbor Laboratory, 1989] or Ausubel et al. [Current Protocols in Molecular Biology, John Wiley & Sons, Inc, 1995], the contents of each of which are herein incorporated by reference. Further, the vectors may be non-fusion vectors (i.e., those producing the enzymes of the invention not fused to any heterologous polypeptide), or alternatively, fusion vectors (i.e., those producing the enzymes fused to a vector encoded polypeptide). The fusion proteins would of course vary with the particular vector chosen. In accordance with a preferred embodiment, the vectors are eukaryotic expression vectors, most preferably plasmids.

Regardless of the specific vector utilized, various sites may be selected for insertion of the isolated nucleotide sequences. These sites are usually designated by the restriction enzyme or endonuclease that cuts them.

The particular site chosen for insertion of the selected nucleotide sequences into the vector to form a recombinant vector is determined by a variety of factors. These include size and structure of the protein to be expressed, susceptibility of the desired protein to enzymatic degradation by the host cell components and contamination by its proteins, expression characteristics such as the location of start and stop codons, and other factors recognized by those of skill in the art. None of these factors alone absolutely controls the choice of insertion site for a particular nucleotide sequence. Rather, the site chosen reflects a balance of these factors, and not all sites may be equally effective for a given protein.

The nucleotide sequences comprising the XI and XKS encoding genes may be inserted into the desired vector by known techniques. If, however, the vector is to serve as an expression vector, the vector should have a promoter effective for expression in the selected host cell, and the nucleotide sequences should be inserted in the vector downstream of the promoter and operationally associated therewith (that is, the promoter should be recognized by the RNA polymerase of the yeast host cell). In addition, the vector should have a region which codes for a ribosome binding site positioned between the promoter and the site at which the nucleotide sequences are inserted so as to be operatively associated with the nucleotide sequences of the invention once inserted (in correct translational reading frame therewith). The vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly(A) tail addition (if eukaryotic). Alternatively, any or all of the above control sequences may be ligated to the coding sequence prior to insertion into the vector.

Nucleic acid constructs may be introduced into the yeast host by numerous methods described in the technical and scientific literature. Transformation of yeast may be performed using standard techniques described in Sambrook et al. (ibid). In general, linear or circular nucleic acid constructs may be introduced into the host by techniques utilizing protoplast fusion, polyethylene glycol, liposomes, lithium acetate, electroporation, physical damage, biolistic bombardment, or *Agrobacterium* mediated transformation.

Successful transformants may be isolated by using markers, contained on the expression vectors, which confer a selectable trait to the transformed yeast host. These may include nutritional selection related to substrate utilization (such as, growth on acetamide containing medium) or prototrophy of a required growth product (such as, arginine, leucine, or uracil). Dominant selectable markers (such as, resistance to ampicillin, G418, hygromycin, and phleomycin) are also useful in selecting transformants that have taken up the introduced DNA construct. Putative successful transformants are preferably further screened for ability to grow on culture medium containing xylose as the sole carbon source. Thus, the selected transformants will express the XI and XKS encoding polynucleotide sequences at a sufficient functional level to be effective to utilize xylose as the sole carbon source.

In accordance with another preferred embodiment, the DNA construct may be replicated autonomously or integrated into the genome of the host. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant. For example, suitable techniques which have been described for multiple chromosomal integration which may be used herein are described by Johansson and Hahn-Hägerdal (2004. Methods Mol. Biol. 267:287-96), Lee and Da Silva (1997a. Applied Microbiology and Biotechnology. 48:339-345), Lee and Da Silva (1997b. Biotechnology Progress. 13:368-373) and Lopes et al. (1989. Gene. 79:199-206), the contents of each of which are incorporated by reference herein.

The recombinant yeast of this invention are effective for the fermentation of sugars from biomass or agricultural wastes to ethanol using conventional techniques. Many processes for the fermentation of monomeric sugars such as glucose generated from lignocellulose are well known, and are suitable for use herein. In brief, the lignocellulosic material may be enzymatically, chemically, and/or physically hydrolyzed to a glucose and xylose containing fraction. Alternatively, the recombinant yeast of this invention may be further transformed with one or more genes encoding for enzymes effective for hydrolysis of complex substrates such as lignocellulose, and include but are not limited to cellulases, hemicellulases, peroxidases, laccases, chitinases, proteases, and pectinases. The glucose and xylose containing hydrolysate is then contacted with the recombinant yeast of this invention under conditions effective for the growth of the yeast on the xylose to produce yeast biomass, and the fermentation of the xylose and/or glucose to ethanol. The growth of the yeast to increase biomass and the ethanol fermentation may be conducted sequentially, in separate stages. In a preferred embodiment, the yeast are propagated under aerobic conditions to increase cell biomass, after which the yeast are cultivated under anaerobic conditions to produce ethanol. Details of the various fermentation techniques, conditions have been described, for example, by Wyman (1994) and Olsson and Hahn-Hägerdal (1996).

After completion of the fermentation, the ethanol may be recovered and optionally purified or distilled. Solid residue containing lignin may be discarded or burned as a fuel.

The following example is intended only to further illustrate the invention and are not intended to limit the scope of the invention which is defined by the claims.

Example 1

Methods
Strains, Media, and General Methods

*Escherichia coli* strain NEB10b (New England Biolabs (NEB); Ipswich, Mass., USA) was used for routine maintenance and preparation of plasmids and were grown in LB medium (Sambrook and Russell, 2001, Molecular Cloning: A Laboratory Manual, 3rd edn., Cold Spring Harbor Laboratory Press, Cold Spring Harbor, N.Y.). DNA was transformed into yeast cells using a standard lithium acetate method (Gietz and Woods, 2002, Methods Enzymol., 350:87-96). Synthetic complete (SC) medium consisted of 6.7 g/l Difco yeast nitrogen base (YNB) (United States Biological; Marblehead, Mass., USA), and was supplemented with amino acids as necessary (Amberg et al., Methods in Yeast Genetics: A Cold Spring Harbor Laboratory Course Manual, 2005 edn., Cold Spring Harbor Laboratory Press, Cold Spring Harbor, N.Y.). YP medium (10 g/l yeast extract, 20 g/l bacto-peptone) was autoclaved without carbohydrate. Sterile glucose or xylose was added separately.

Cloning of the *Prevotella ruminicola* TC2-24 Xylose Isomerase

The rumen bacterium *Prevotella ruminicola* TC2-24 was grown anaerobically at 37° C. in RGM medium as described in (Hespell et al., 1987, Appl. Environ. Microbiol., 53:2849-2853). Cells were harvested by centrifugation, washed once with sterile water and harvested again. Genomic DNA was prepared from cells using the QuickExtract Bacterial DNA Extraction Kit (Epicentre; Madison, Wis., USA) according to the instructions. The *Prevotella ruminicola* TC2-24 xylose isomerase gene was obtained by PCR amplification using genomic DNA and primers SpeI-PrevXI-F (5'-GCACTAGTATGGCAAAAGAGTATTTCCC-3' SEQ ID NO: 7) and SalI-PrevXI-R (5'-CCGTCGACTTACTTGCAGTAAAGTGCTACG-3' SEQ ID NO: 8). Advantage Taq (CloneTech; Mountain View, Calif., USA) was used per manufacturer's instructions using the following program: 95° C. for 1 min, 14 cycles of 95° C. for 30 s, 60° C. for 20 s (decreasing 1° C. per cycle), and 68° C. for 1 min 30 s, 19 cycles of 95° C. for 30 s, 45° C. for 20 s, and 68° C. for 1 min 30 s, 70° C. for 10 min. PCR products were separated by agarose gel electrophoresis. DNA fragments from 1.0 to 1.5 kb range were removed from the gel and purified using a QIAquick Gel Extraction Kit (Qiagen, Valencia, Calif.). Terminal adenosines were added to the DNA fragments by incubation with HotMaster Taq (SPrime, Gaithersburg, Md.). DNA fragments were then cloned into pCR2.1 and transformed into *E. coli* NEB10B cells (New England Biolabs). The DNA fragments were sequenced using M13 forward and reverse primers. Vectors containing xylose isomerase-like sequences were digested with restriction enzymes SpeI and EcoRI and the xylose isomerase gene was cloned into the yeast expression vector pRH167 using the same restriction enzymes to create vector pRH367. The yeast expression vector contains the truncated HXT7 promoter and HXT7 terminator sequences allowing constitutive high-level expression in *S. cerevisiae*.

Construction of Yeast Expression Vectors

Yeast expression vectors were generated by PCR amplification of the HXT7 promoter from *S. cerevisiae* genomic DNA using primers HXT7p SacI-F (5'-TAGGAGCTCTTTCGGGCCCCTGC-3' SEQ ID NO: 9) and HXT7p SpeI-R (5'-AGCGTCTTGTGACTAGTTTTGATT-3' SEQ ID NO: 10). The HXT7 terminator was separately amplified using primers HXT7t SalI-F (5' GGTCGACGCGAACACTTTTATTAATTC-3' SEQ ID NO: 11) and HXT7t XhoI-R (5'-GCTCGAGTATTTGTGAATAACAGTGCGGTC SEQ ID NO: 12). DNA fragments for cloning were amplified using PfuTurbo Hotstart polymerase (Stratagene; La Jolla, Calif., USA). Adenosine overhangs were added with Taq polymerase (NEB) and each fragment was cloned into pCR2.1 (Invitrogen) and sequenced. Error-free promoter and terminator fragments were sub-cloned into vectors pRS414 and pRS416 (Christianson et al., 1992, Gene, 110:119-122) using restriction enzyme sites that were incorporated into the primer sequence.

Codon Optimization

*P. ruminicola* XI and XKS genes optimized for expression in *S. cerevisiae* ((SEQ ID NO: 3) and (SEQ ID NO: 6) respectively) were synthesized (DNA2.0; Menlo Park, Calif., USA). Restriction enzyme sites were included at the 5' and 3' ends of the synthesized DNA sequence to facilitate cloning. The optimized genes were then cloned into the yeast expression vectors described above and transformed into the yeast strain CEN.PK2-1C.

Xylose Isomerase Assay

Clarified cell lysates were prepared from cells grown to mid-log phase. Cells were collected by centrifugation, washed once with sterile water, resuspended in an appropriate amount of Y-PER reagent (Pierce; Rockford, Ill., USA) plus protease inhibitors (Complete, mini, EDTA-free protease inhibitor cocktail, Roche; Indianapolis, Ind., USA), and processed according to the instructions. Protein concentrations were determined with the Quick Start Bradford Protein Assay (Bio-Rad; Hercules, Calif., USA) against a bovine serum albumin standard. Xylose isomerase activity was assayed in buffer containing 100 mM Tris-HCl, pH 7.5, 10 mM $MgCl_2$, 2 units of sorbitol dehydrogenase, 0.15 mM NADH, and an appropriate amount of lysate. Reactions were performed in 1 ml volume at 25° C. and were started by the addition of xylose. Reactions were monitored by following NADH absorbance at 340 nm and specific activity was determined in µmoles/min/mg of protein. The molar absorption coefficient, $\epsilon_{340}$, was 6.22 $mM^{-1}$ $cm^{-1}$ for NADH. A Cary 50 Bio UV-Visible spectrophotometer (Varian; Palo Alto, Calif., USA), was used for spectral and kinetic determinations. $K_m$ and $V_{max}$ values were determined from Hanes-Woolf plots with xylose concentrations from 500-10 mM.

Aerobic Growth Determination

Pre-cultures were grown to exponential phase in SC+20 g/L glucose and lacking amino acids as required for plasmid maintenance. Synthetic complete medium+50 g/l xylose (SC5X) was used to determine each strain's ability to assimilate xylose aerobically. Cultures were started at an $OD_{660}$ of 0.05 and incubated at 30° C., shaking at 200 rpm. *S. cerevisiae* transformed with both of the *Prevotella* XI and XKS of this invention was compared with *S. cerevisiae* transformed with XI and XKS from other sources. The results are shown in FIG. 7.

Batch Fermentation

Figure 8:
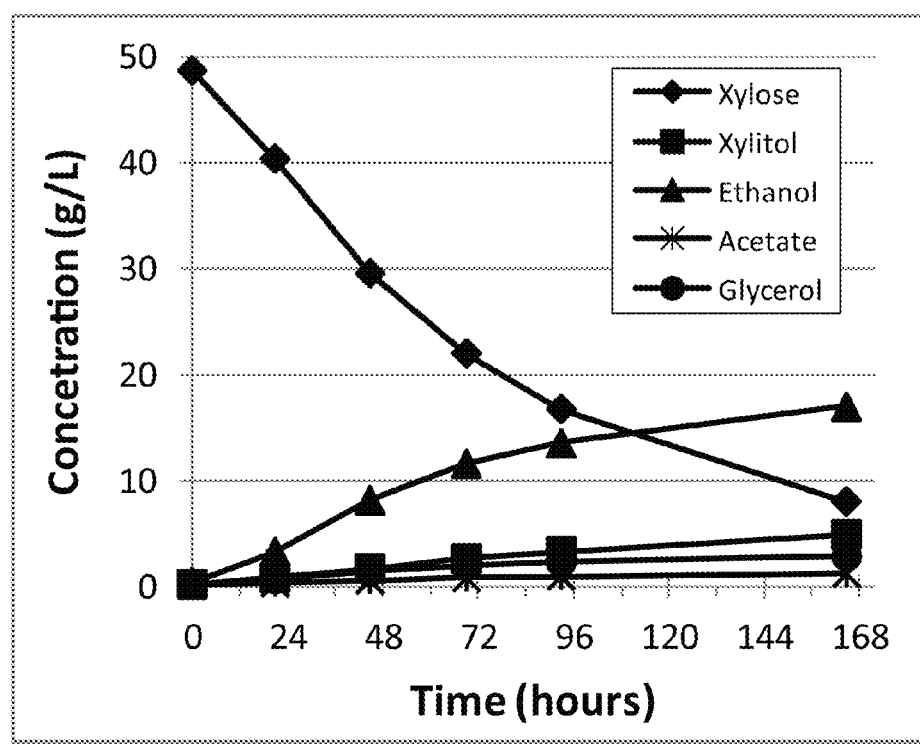
FIG. 8 shows xylose consumption and production of fermentation products formed during the batch culture on xylose medium by recombinant *S. cerevisiae* expressing the *P. ruminicola* XI and XKS as described in Example 1.

Xylose fermentation was investigated by inoculating 100-ml cultures using YP+50 g/L xylose at a starting $OD_{660}$ of 5. Exponentially growing cells were used for the inoculum. Flasks were sealed with a rubber stopper and pierced with a 22G. needle to vent $CO_2$ produced during the fermentation. Samples were taken every 24 hours to determine cell biomass (by $OD_{660}$) and analyze remaining sugars and products formed (by high-performance liquid chromatography, HPLC). The results are shown in FIG. 8. The recombinant *S. cerevisiae* strain expressing codon-optimized *P. ruminicola* XI and XK had a theoretical ethanol yield of 8% (at 93 hours). A recombinant *S. cerevisiae* strain expressing the *S. stipitis* reductase/dehydrogenase pathway for xylose utilization only achieves 50% theoretical ethanol yield under identical conditions, due to excessive production of xylitol (not shown).

Analytical Methods

Extracellular metabolites were measured using HPLC. Samples were analyzed using a SpectraSYSTEM liquid chromatography system (Thermo Electron Corporation, CA, USA) equipped with an automatic sampler, column heater, isocratic pump, refractive index detector, and computer-based integrator running Chromquest ver. 2.5 software (Thermo Electron Corporation). Samples were injected (20 μl) onto a sugar column (Aminex HPX-87H Column, 300 9 7.8 mm, Bio-Rad Laboratories, Inc.) and eluted with 5 mM sulfuric acid at 0.6 ml/min and 65° C.

It is understood that the foregoing detailed description is given merely by way of illustration and that modifications and variations may be made therein without departing from the spirit and scope of the invention.

We claim:

1. A nucleic acid construct comprising an isolated nucleic acid molecule comprising a nucleic acid sequence encoding a xylose isomerase, wherein said xylose isomerase comprises the amino acid sequence of SEQ ID NO: 1, said nucleic acid molecule being operably linked to one or more expression control sequences.

2. The nucleic acid construct of claim 1 wherein said nucleic acid sequence is selected from the group consisting of SEQ ID NO: 2 and SEQ ID NO: 3.

3. The nucleic acid construct of claim 1 further comprising a second nucleic acid sequence encoding a xylulokinase.

4. The nucleic acid construct of claim 3 wherein said xylulokinase comprises the amino acid sequence of SEQ ID NO: 4.

5. The nucleic acid construct of claim 4 wherein said second nucleic acid sequence is selected from the group consisting of SEQ ID NO: 5 and SEQ ID NO: 6.

6. A yeast cell transformed with the nucleic acid construct of claim 1.

7. A yeast cell transformed with the nucleic acid construct of claim 2.

8. A yeast cell transformed with the nucleic acid construct of claim 3.

9. A yeast cell transformed with the nucleic acid construct of claim 4.

10. The yeast cell of claim 6 further transformed with a second nucleic acid construct comprising a nucleic acid molecule comprising a nucleic acid sequence encoding a xylulokinase operably linked to one or more expression control sequences.

11. The yeast cell of claim 10 wherein said xylulokinase comprises the amino acid sequence of SEQ ID NO: 4.

12. The yeast cell of claim 11 wherein said nucleic acid sequence encoding said xylulokinase is selected from the group consisting of SEQ ID NO: 5 and SEQ ID NO: 6.

13. The yeast cell of claim 6 wherein said yeast is a *Saccharomyces* species.

14. The yeast cell of claim 13 wherein said yeast is *Saccharomyces cerevisiae*.

* * * * *

SEQUENCE LISTING

```
<160> NUMBER OF SEQ ID NOS: 12

<210> SEQ ID NO 1
<211> LENGTH: 439
<212> TYPE: PRT
<213> ORGANISM: Prevotella ruminicola

<400> SEQUENCE: 1

Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Glu Pro Glu Lys
                20                  25                  30

Val Val Met Gly Lys Lys Met Lys Asp Trp Leu Lys Phe Ala Met Ala
            35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
            100                 105                 110

Ile Ala Glu Tyr Glu Arg Arg Met Lys Glu Ile Thr Asp Tyr Ala Leu
        115                 120                 125

Val Lys Met Lys Glu Tyr Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Cys Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Asn Gly Met Leu Gly Ser Ile Asp Ala Asn Arg Gly Asp Ala
    290                 295                 300

Gln Asn Gly Trp Asp Thr Asp Gln Phe Pro Ile Asp Asn Phe Glu Leu
305                 310                 315                 320

Thr Gln Ala Met Leu Glu Ile Ile Arg Asn Gly Gly Leu Gly Asn Gly
                325                 330                 335
```

```
Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Met Asn Ala Ala Ala Ile Leu Glu Glu Ser Glu Leu Pro Lys Met
    370                 375                 380

Lys Lys Glu Arg Tyr Ala Ser Phe Asp Asn Gly Ile Gly Lys Asp Phe
385                 390                 395                 400

Glu Asp Gly Lys Leu Thr Leu Glu Gln Ala Tyr Glu Tyr Gly Lys Lys
                405                 410                 415

Val Glu Glu Pro Lys Gln Thr Ser Gly Lys Gln Glu Lys Tyr Glu Thr
            420                 425                 430

Thr Val Ala Leu Tyr Cys Lys
            435
```

<210> SEQ ID NO 2
<211> LENGTH: 1320
<212> TYPE: DNA
<213> ORGANISM: Prevotella ruminicola

<400> SEQUENCE: 2

```
atggcaaaag agtatttccc gtttaccggt aaaattcctt tcgagggaaa ggacagtaag      60
aatgtaatgg ctttccacta ttacgagcct gagaaggtcg tgatgggaaa gaagatgaag     120
gactggctga agttcgctat ggcttggtgg catacactgg gtggcgcttc tgctgaccag     180
tttggtggtc agactcgttc ttatgagtgg gataaggctg ctgacgccgt tcagcgcgca     240
aaggataaga tggacgctgg ttttgagatc atggacaagc tgggtatcga gtacttctgc     300
ttccacgatg ttgacctcgt tgaagagggt gagacgatcg ctgagtacga cgtcgcatg      360
aaggagatca cagactacgc tctggtgaag atgaaggaat atcccaacat caagctcctc     420
tggggtacag ctaacgtatt tggcaacaag cgctatgcaa atggtgcttc taccaaccct     480
gatttcgacg ttgtggctcg cgccatcgtt cagatcaaga cgctatcga tgctaccatc      540
aagttgggtg gtaccaacta tgtattctgg ggcggtcgtg agggttatat gagccttctg     600
aacactgacc agaagcgtga agggagcac atggcaacca tgctgaccat ggctcgcgac      660
tacgctcgcg ctaagggctt caagggtacg ttcctgattg agccgaagcc catggagcct     720
tcaaagcacc agtacgatgt tgacactgag accgtatgcg gtttcctccg tgctcatggt     780
ctggacaagg acttcaaggt gaacatcgag gtaaaccacg ctactctggc aggtcacacc     840
ttcgagcacg agctggcttg cgctgtcgac aacggtatgc tcggttctat cgacgctaac     900
cgtggtgatg ctcagaacgg ttgggatact gaccagttcc ccatcgacaa cttcgagctg     960
acacaggcta tgctggagat catccgcaat ggtggtctgg gcaatggcgg taccaacttc    1020
gacgctaaga tccgtcgtaa ctctaccgac ctcgaggatc tcttcatcgc tcacatcagc    1080
ggtatggatg ctatggcacg cgccctgatg aatgctgctg ctatcctgga ggagagcgag    1140
ctgccgaaga tgaagaagga gcgttatgct tcattcgaca acggtattgg taaggacttc    1200
gaggatggca agctgactct cgagcaggct tacgagtacg gtaagaaggt tgaggagccc    1260
aagcagactt ctggtaagca ggagaagtac gagaccaccg tagcactttat ctgcaagtaa   1320
```

<210> SEQ ID NO 3
<211> LENGTH: 1320
<212> TYPE: DNA
<213> ORGANISM: Prevotella ruminicola -continued

<400> SEQUENCE: 3

```
atggccaaag agtacttccc attcaccgga aagataccat tcgaaggcaa agattccaaa      60
aacgtgatgg cctttcacta ttacgaacca gaaaaagtcg ttatgggcaa aaagatgaaa     120
gattggctga aattcgccat ggcttggtgg catacactag gtggcgcatc tgcagaccaa     180
ttcggaggtc aaactagatc ttatgaatgg gataaagcag ctgacgctgt acagagagca     240
aaagataaga tggatgcagg gttcgagatc atggataagc ttggtattga atacttttgt     300
tttcatgacg ttgacttagt ggaggaaggc gagactattg cagagtacga acgtagaatg     360
aaggaaatca ctgattatgc tttagtcaag atgaaggaat acccaaacat taagttgttg     420
tgggggacag ctaatgtttt tggcaacaaa agatacgcta atggagcctc aacaaatcct     480
gattttgatg tagttgccag ggccatcgtt caaatcaaaa acgcaattga cgcaacaatc     540
aaattgggag gtacaaacta cgttttctgg ggtggaaggg agggttacat gtcattgctg     600
aatactgatc agaaaagaga aaaggaacat atggccacta tgcttactat ggccagagac     660
tacgcaagag ctaagggttt caagggtact tttctaattg agcctaaacc tatggaacct     720
tctaaacatc aatacgatgt agataccgag acagtctgtg gttttctaag agctcacggc     780
ttagataaag actttaaggt aaacattgaa gttaatcacg caactctggc tggtcataca     840
tttgagcatg aattggcatg tgctgtggac aatggaatgc ttggctctat cgatgcaaat     900
agaggtgacg cacaaaatgg gtgggatacc gatcagtttc caatcgacaa ctttgaacta     960
actcaagcaa tgttggaaat cattagaaat ggggggattag gtaatggtgg aacaaacttt    1020
gatgctaaga tacgtagaaa ttccacagac ttggaagatt tgttcatagc tcacattagt    1080
ggcatggatg ctatggcaag agccctaatg aacgctgctg caatacttga ggaatcagaa    1140
ttgccaaaga tgaaaaagga gagatatgct tcatttgaca atggtatcgg taaagatttc    1200
gaagatggta aacttacatt agaacaagct tacgaatatg gcaaaaaggt tgaggaacca    1260
aagcaaacct ctggtaaaca agagaaatac gaaacaaccg tggccctgta ttgcaagtaa    1320
```

<210> SEQ ID NO 4
<211> LENGTH: 496
<212> TYPE: PRT
<213> ORGANISM: Prevotella ruminicola

<400> SEQUENCE: 4

```
Met Ala Asn Arg Tyr Leu Leu Gly Phe Asp Val Gly Ser Ser Val
1               5                   10                  15

Lys Ala Ser Leu Val Asn Ala Asp Ser Gly Lys Cys Val Ala Thr Ala
            20                  25                  30

Phe Tyr Pro Glu Lys Glu Ala Pro Ile Met Ala Val Lys Ala Gly Trp
        35                  40                  45

Ala Glu Gln Asp Pro Gln Met Trp Trp Asp Asn Ala Lys Leu Ser Leu
    50                  55                  60

Gln Lys Ile Met Lys Glu Ser Gly Ala Thr Ala Glu Glu Ile Lys Ala
65                  70                  75                  80

Val Gly Ile Ser Tyr Gln Met His Gly Leu Val Cys Val Asp Lys Asp
                85                  90                  95

Leu Lys Ala Leu Arg Pro Ala Ile Ile Trp Cys Asp Ser Arg Ala Val
            100                 105                 110

Pro Tyr Gly Glu Lys Ala Phe Lys Asp Leu Gly Ala Asp Lys Cys Leu
        115                 120                 125

Ser His Leu Leu Asn Ser Pro Gly Asn Phe Thr Ala Ala Lys Leu Ala
    130                 135                 140
```

Trp Val Lys Glu Asn Glu Pro Glu Leu Tyr Ser Lys Ile Tyr Lys Val
145                 150                 155                 160

Met Leu Pro Gly Asp Tyr Ile Ala Met Arg Leu Ser Gly Val Ala Asn
            165                 170                 175

Thr Thr Val Ser Gly Leu Ser Glu Gly Met Phe Trp Asp Phe Lys Asn
            180                 185                 190

Asn Gln Val Ala Asp Phe Leu Met Asp Tyr Tyr Gly Phe Asp His Ser
        195                 200                 205

Leu Ile Ala Asp Ile Val Pro Thr Phe Ala Glu Gln Ser Val Val Ser
    210                 215                 220

Ala Glu Ala Ala Glu Met Gly Leu Lys Ala Gly Thr Pro Ile Thr
225                 230                 235                 240

Tyr Arg Gly Gly Asp Gln Pro Asn Asn Ala Leu Ser Leu Asn Val Leu
                245                 250                 255

Asn Pro Gly Glu Ile Ala Ala Thr Ala Gly Thr Ser Gly Val Val Tyr
            260                 265                 270

Gly Val Leu Gly Asp Val Asn Tyr Asp Pro Gln Ile Arg Val Asn Thr
        275                 280                 285

Phe Ala His Val Asn His Thr Ala Asp Gln Thr Arg Leu Gly Val Leu
    290                 295                 300

Leu Cys Ile Asn Gly Thr Gly Ile Leu Asn Ala Trp Thr His Arg Asn
305                 310                 315                 320

Ile Thr Pro Glu Ile Gly Tyr Ala Glu Met Asn Asp Leu Ala Ala Ser
                325                 330                 335

Val Pro Ile Gly Ser Glu Gly Val Thr Val Ile Pro Phe Gly Asn Gly
            340                 345                 350

Ala Glu Arg Val Leu Glu Asn Lys Glu Ile Gly Cys Ser Ile Asn Gly
        355                 360                 365

Leu Asn Phe Asn Lys His Asn Lys Ala His Leu Val Arg Ala Ala Gln
    370                 375                 380

Glu Gly Ile Val Phe Ser Phe Cys Tyr Gly Met Glu Ile Met Gln Gln
385                 390                 395                 400

Met Gly Met Asp Ile Lys Lys Ile His Ala Gly Lys Ala Asn Met Phe
                405                 410                 415

Leu Ser Pro Leu Phe Arg Asn Thr Leu Ala Gly Val Ser Gly Ala Thr
            420                 425                 430

Ile Glu Leu Tyr Asp Thr Asp Gly Ser Val Gly Ala Ala Lys Gly Ala
        435                 440                 445

Gly Leu Gly Ala Gly Ile Tyr Ala Asn Ala Ser Glu Ala Phe Ala Ser
    450                 455                 460

Leu Asp Lys Leu Glu Val Ile Glu Pro Asp Ala Gln Asn Arg Ala Ala
465                 470                 475                 480

Tyr Arg Ala Ala Tyr Glu Ala Trp Lys Glu Thr Leu Lys Lys Asn Met
                485                 490                 495

<210> SEQ ID NO 5
<211> LENGTH: 1491
<212> TYPE: DNA
<213> ORGANISM: Prevotella ruminicola

<400> SEQUENCE: 5
atggcaaata gatatctatt aggttttgat gtcggtagct catcagtgaa ggcatcgttg    60
gttaacgccg atagcggcaa gtgtgtggca acagcttttt atcctgaaaa ggaggctcct   120
attatggctg taaaggctgg atgggcagag caggatccac agatgtggtg ggataatgcc   180

```
aaattgagtc tgcagaagat tatgaaagag agtggtgcta cagctgagga gattaaggct    240
gtgggtatct cgtatcagat gcacggtttg gtttgtgtag ataaggatct gaaggcattg    300
cgtccagcta ttatttggtg cgactcacgt gctgtacctt atggcgagaa ggctttcaag    360
gatctcggtg ctgacaagtg cttgagtcat ctgttgaatt caccaggaaa ctttaccgct    420
gccaagttgg cttgggtaaa agaaaatgaa ccagaactct atagtaaaat atataaggta    480
atgctgcctg gtgattatat cgctatgcga ctgagtggtg ttgctaatac cactgtcagc    540
ggtctgtcag agggtatgtt ctgggatttc aagaataatc aggtggctga cttcttgatg    600
gattactatg gattcgatca ttcgctgatt gctgatatcg ttccaacctt tgctgagcag    660
agcgtagtaa gtgcagaagc tgctgctgag atgggcctga agctggtac tcctatcacc     720 tatagaggtg gtgaccagcc aaacaatgcg ctctcgctga atgtgctgaa tcctggtgag    780
attgctgcaa ctgcaggtac atcgggtgtg gtttatggtg tacttggtga tgtgaactac    840
gatccacaga tccgtgtaaa acttttgca catgtgaatc atacagcaga ccagactcgt     900
ctgggagtgc tgcttttgtat taatggtact ggtattttga atgcttggac tcatcgtaat   960
atcacgccta agattggcta tgccgagatg aacgatctgg ctgccagtgt gcccattggt    1020
agtgagggcg tgactgtaat tccattcgga aatggtgctg agcgcgtatt ggagaacaag    1080
gagattggtt gttctatcaa tggcttgaac tttaataagc ataacaaggc tcacttggtt    1140
cgtgctgctc aggagggtat cgtattctca ttctgctatg gtatggagat tatgcagcag    1200
atgggtatgg atattaagaa gattcacgct ggtaaggcta acatgttctt gagtccattg    1260
ttccgtaata cattggctgg tgtgagtggt gcaaccatcg aactgtatga tacagatggt    1320
tcggtaggta ccgccaaggg tgctggctta ggtgctggca tctatgctaa tgcttctgag    1380
gcttttgctt cgctggataa gttggaggtg attgagccag atgctcagaa ccgcgctgct    1440
taccgtgctg cctatgaggc ttggaaagaa accttgaaaa agaatatgta a             1491

<210> SEQ ID NO 6
<211> LENGTH: 1491
<212> TYPE: DNA
<213> ORGANISM: Prevotella ruminicola

<400> SEQUENCE: 6
atggcaaaca gatacttgct ggggttcgat gttggttcct ctagtgtaaa agcatcttta     60
gttaacgctg atagtgggaa atgtgtagca acagcattct atccagaaaa ggaagctcct    120
atcatggctg ttaaagcagg atgggctgaa caagatccac aaatgtggtg ggataatgcc    180
aagttgtctt tacagaaaat catgaaggaa tccggagcta cagccgagga gattaaggcc    240
gttggcatat cataccaaat gcatggattg gtttgcgtag ataaagatct aaaagctcta    300
cgtcctgcaa tcatttggtg tgactccaga gctgtcccat atggtgaaaa agccttttaag  360 gacttaggtg ccgataagtg tttgtcacat ttgttaaaca gtccaggcaa tttcacagca    420
gctaagttag cctgggtaaa ggaaaatgaa ccagaattgt actcaaagat atacaaagtc    480
atgctaccag gtgattacat cgcaatgaga ctttctgggg tagcaaatac tacagtgtct    540
ggattatctg aaggaatgtt ttgggatttc aaaaacaatc aagtagctga ctttctgatg    600
gactattacg gttttgacca ttcacttatt gctgatatag tccctacttt tgcagaacaa    660
tcagtcgtat ctgccgaggc agccgcagaa atgggtctaa aggcaggtac tcctattacc    720
tatagaggtg gcgatcaacc taacaatgct ttaagtttga acgtgcttaa tccaggtgag    780
attgctgcca cagctggtac atctggtgtt gtgtatggtg ttttaggtga cgtgaattac    840
```

```
gatccacaga taagagtgaa tacttttgcc cacgttaatc ataccgctga ccagactagg    900
ttaggtgttc tgctttgtat caacggaaca ggcatcctga atgcctggac acatagaaac    960
attactccag aaataggtta cgctgaaatg aacgatctag ctgcttcagt accaattggg   1020
tctgagggcg ttacagttat cccattcggt aatggagctg aaagggtctt ggagaataag   1080
gaaatagggt gttcaatcaa tggtctgaac tttaacaaac acaacaaagc tcaccttgtg   1140
agagccgctc aggaaggaat agtctttcca ttttgctatg gtatggaaat catgcaacaa   1200
atgggaatgg acatcaaaaa gattcatgcc ggaaaagcaa acatgttcct atctcctttg   1260
tttagaaata ctttagctgg agtttcagga gctaccattg agttatacga cacagatggt   1320
tccgttggcg cagcaaaagg cgcaggcttg ggtgccggca tctacgccaa tgcatctgaa   1380
gctttcgctt ctcttgataa acttgaagtg atcgaacctg acgctcaaaa cagagccgct   1440
tatagagccg catacgaagc atggaaagag actttgaaaa agaacatgta a            1491
```

<210> SEQ ID NO 7
<211> LENGTH: 28
<212> TYPE: DNA
<213> ORGANISM: Prevotella ruminicola

<400> SEQUENCE: 7

```
gcactagtat ggcaaaagag tatttccc                                       28
```

<210> SEQ ID NO 8
<211> LENGTH: 30
<212> TYPE: DNA
<213> ORGANISM: Prevotella ruminicola

<400> SEQUENCE: 8

```
ccgtcgactt acttgcagta aagtgctacg                                     30
```

<210> SEQ ID NO 9
<211> LENGTH: 23
<212> TYPE: DNA
<213> ORGANISM: Saccharomyces cerevisiae

<400> SEQUENCE: 9

```
taggagctct ttcgggcccc tgc                                            23
```

<210> SEQ ID NO 10
<211> LENGTH: 24
<212> TYPE: DNA
<213> ORGANISM: Saccharomyces cerevisiae

<400> SEQUENCE: 10

```
agcgtcttgt gactagtttt gatt                                           24
```

<210> SEQ ID NO 11
<211> LENGTH: 27
<212> TYPE: DNA
<213> ORGANISM: Saccharomyces cerevisiae

<400> SEQUENCE: 11

```
ggtcgacgcg aacacttttta ttaattc                                       27
```

<210> SEQ ID NO 12
<211> LENGTH: 30
<212> TYPE: DNA
<213> ORGANISM: Saccharomyces cerevisiae -continued

<400> SEQUENCE: 12
gctcgagtat ttgtgaataa cagtgcggtc                30